Figure 1:
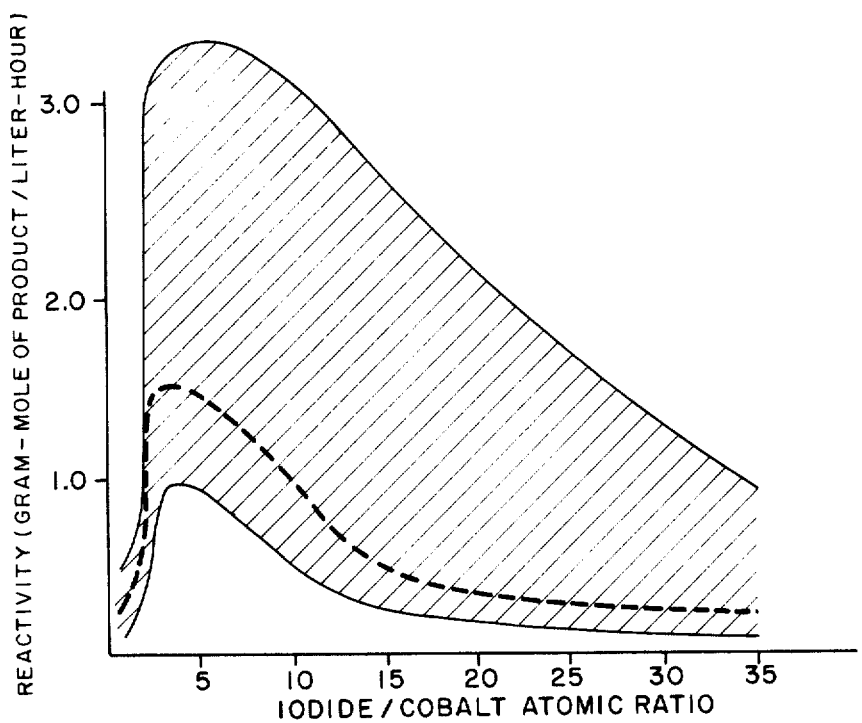

United States Patent [19]

Hershman et al.

[11] 3,944,604
[45] Mar. 16, 1976

[54] PRODUCTION OF PROPIONIC ACID

[75] Inventors: Arnold Hershman, Creve Coeur; Denis Forster, University City, both of Mo.

[73] Assignee: Monsanto Company, St. Louis, Mo.

[22] Filed: Aug. 21, 1973

[21] Appl. No.: 390,268

[52] U.S. Cl....... 260/533 A; 252/429 B; 252/431 P; 252/431 N; 260/497 R
[51] Int. Cl.² ........................... C07C 51/14
[58] Field of Search .............................. 260/533 A

[56] References Cited
UNITED STATES PATENTS

| | | | |
|---|---|---|---|
| 1,957,939 | 5/1934 | Carpenter | 260/533 A |
| 2,593,440 | 4/1952 | Hagemeyer, Jr. | 260/533 A |
| 2,710,878 | 6/1955 | Glasebrook | 260/533 A |
| 2,710,879 | 6/1955 | Snyder | 260/533 A |
| 2,739,169 | 3/1956 | Hagemeyer | 260/533 A |
| 2,882,297 | 4/1959 | Luberoff | 260/533 A |
| 2,882,298 | 4/1959 | Luberoff | 260/533 A |
| 3,579,551 | 5/1971 | Craddock et al. | 260/533 A |

Primary Examiner—Lorraine A. Weinberger
Assistant Examiner—Paul J. Killos

[57] ABSTRACT

The present invention relates to an improved process for the preparation of propionic acid, specifically by the reaction of ethylene with carbon monoxide and water at mild pressure, in the presence of catalyst compositions essentially comprising critical proportions of cobalt compounds with an iodide promoter.

10 Claims, 2 Drawing Figures

PRODUCTION OF PROPIONIC ACID

This invention relates to an improved process for the production of propionic acid. More particularly, it relates to a process for the reaction of ethylene with carbon monoxide and water in the presence of catalyst compositions essentially comprising critical ratios of cobalt compounds and complexes and an iodide promoter to yield propionic acid selectively and efficiently at mild pressure.

Processes for the preparation of carboxylic acids from olefins, and other ethylenically unsaturated compounds, carbon monoxide and water are well known in the art and have been directed to the production of carboxylic acids and ester derivatives. The prior art teaches the use of a number of catalysts for the synthesis of carboxylic acids by reaction of olefins with carbon monoxide and water at elevated temperatures and pressures. Catalysts such as phosphoric, boric, arsenic and monochloroacetic acids; acetyl chloride on active carbon; boron trifluoride; barium and calcium halides; salts and carbonyls of nickel and cobalt, especially halides; and in general, the Group VIII metals, and simple salts, carbonyls and complexes; have been reported to function for the production of carboxylic acids and esters by reaction of olefins and carbon monoxide in the presence of water or other hydroxylic compounds at temperatures from 130°C – 375°C and pressures up to 1,000 atmospheres. However, even under such severe conditions the yields of acid were substantially poor, and therefore, uneconomical. Somewhat less severe reaction conditions of temperature and/or pressure have been reported in the literature employing specific catalyst compositions, e.g., 200°C to 300°C and 150 to 200 atmospheres in the presence of 87% phosphoric acid; 300°C to 375°C and 450 to 740 atmospheres in the presence of nickel carbonyl promoted by nickel chloride and hydrochloric acid; or 85°C to 250°C and 100 to 1,000 atmospheres in the presence of palladium phosphine complex catalysts.

Even using the prior art specific catalyst compositions and reaction conditions, substantially poorer yields of the desired carboxylic acid product and substantially slower reaction rates are obtained than those achieved in the process of this invention.

Certain disadvantages present in the carbonylation processes described in the prior art are catalyst instability, lack of product selectivity, low levels of catalyst reactivity and high levels of halide promoter required. One particular disadvantage of olefin carbonylation processes of the prior art is their dependence upon the use of catalysts comprised of metal carbonyls or certain modified metal carbonyls which do not have critical proportions of iodide present including dicobalt octacarbonyl, iron carbonyl and nickel carbonyl, all of which require the use of high partial pressures of carbon monoxide to remain stable under the necessarily high reaction temperatures employed. For example, dicobalt octacarbonyl requires partial pressures of carbon monoxide as high as 3,000 psig to 10,000 psig under normal carbonylation conditions of 175°C to 300°C. Furthermore the present carbonylation process to propionic acid requires water as a reactant. For a dicobalt octacarbonyl catalyst the water would cause decomposition of the octacarbonyl with resultant precipitation of the cobalt metal.

Another disadvantage of these metal carbonyl catalyst systems such as nickel carbonyl is their volatility at reaction conditions. Thus expensive metal recovery equipment is required to maintain the metal in the reactor or recycle the metal component to the reactor after catalyst separation.

Still another disadvantage of carbonylation processes for ethylenically unsaturated compounds disclosed in the prior art is their relatively low level of activity. This low level of activity requires higher catalyst concentrations, higher halogen concentrations, longer reaction times, and higher temperatures to obtain substantial reaction rates and conversions. Consequently, very large and costly processing equipment is required.

Still another disadvantage of carbonylation processes of the prior art for producing carboxylic acid from olefins is the necessity of using extremely high partial pressures of carbon monoxide of the order of 1500 to 15,000 psig to accomplish efficient reaction when high concentrations and high ratios of halide promoter (expressed as atoms of halide per atom of metal catalyst moiety) are employed with both Group VIII, first row (iron, cobalt and nickel), and noble metals as catalysts.

Another disadvantage of carbonylation processes disclosed heretofore, which employ feedstocks having ethylenically unsaturated linkages, is their inability to maintain high selectivity to the desired carboxylic acid at temperatures and halogen promoter levels required for high conversion levels and high reaction rates. At these higher temperatures and higher halide promoter concentrations undesirable byproducts comprising substantial amounts of ethers, aldehydes, ketones, lactones, esters, higher carboxylic acids and alcohols, carbon dioxide, methane and water are formed, thereby resulting in substantial yield losses and necessitating additional product purification and recycle steps in the processing.

It is therefore, an object of the present invention to overcome the above disadvantages and thus provide an improved and more economically and commercially feasible carbonylation process for the production of propionic acid from ethylene, in liquid phase and vapor phase processes at low pressure.

Another object of this invention is to provide a more reactive, less volatile, more stable carbonylation catalyst composition than has been heretofore described in the prior art.

Still another object of the present invention is to provide a more selective and more reactive carbonylation catalyst composition for the production of propionic acid from ethylene.

Another object of the present invention is to provide a carbonylation catalyst composition which results in the production of a higher yield of the desired carboxylic acid with no substantial formation of ethers, aldehydes, ketones, lactones, higher carbon number carboxylic acids and alcohols, carbon dioxide, methane, water and other undesirable byproducts.

Still another object of the present invention is the provision of an improved carbonylation process enabling the efficient and selective production of propionic acid by reaction of ethylene with carbon monoxide and water at low pressure in the presence of an improved and more stable catalyst, thus enabling the use of lower catalyst concentration, lower temperature, and shorter contact time than has been generally possible heretofore.

In accordance with the present invention superior yields of propionic acid are obtained by reaction of ethylene in the liquid phase or vapor phase with carbon monoxide and water at temperatures from about 50°C to 300°C, preferably 125°C to 225°C, and at partial pressures of carbon monoxide from 1 psia to 1500 psia, preferably 25 psia to 800 psia although higher pressure may be employed, in the presence of a catalyst system comprising a cobalt containing component, and an iodide promoter portion used in critical ratios defined herein. The present process is particularyly advantageous at lower pressure, although higher pressures may also be used.

For purposes of the present invention, the catalyst system essentially includes both cobalt and iodide components. Generally, the cobalt component of the catalyst system of the present invention is believed to be present in the form of a coordination compound of cobalt with an iodide component providing at least one of the ligands of such coordination compound. In addition to the cobalt and iodide, in the process of the present invention, these coordination compounds also generally include carbon monoxide ligands. Other moieties may be present if desired. Generally it is preferred that the catalyst system contain as a promoting component, an excess of iodide over that present as ligands in the coordination compound. The terms "coordination complex" used throughout this specification means a compound or complex formed by combination of one or more electronically rich molecules or atoms capable of independent existence with one or more electronically poor molecules or atoms, each of which may also be capable of independent existence.

The essential cobalt and iodide components of the catalyst system of the present invention may be provided by introducing into the reaction zone a coordination compound of cobalt containing iodide ligands or may be provided by introducing into the reaction zone separately a cobalt compound and an iodide compound. Among the materials which may be charged to the reaction zone to provide the metal component of the catalyst system of the present invention are cobalt metal, cobalt salts and oxides, organo cobalt compounds, coordination compounds of cobalt and the like. Specific examples of materials capable of providing the metal constituent of the catalyst system of the present invention may be taken from the following non-limiting partial list of suitable materials. Chemical and/or physical treatment of the metal precursor may be desirable as discussed below, in order to render the cobalt moiety in the proper valence state and ligand environment. For example, cobalt complexes containing stable chelating ligands, such as trisacetylacetonato cobalt (III), may be treated chemically to remove or destroy the bidentate chelate ligands in order that transformation to the proper valence state and ligand configuration can be accomplished.

Also in the presence of certain biphyllic ligands detrimental effects have been observed on reaction rate employing the cobalt/iodide catalyst sytem for propionic acid production. In contradistinction to other Group VIII metal catalyst systems which require biphyllic ligands e.g. (triphenylphosphine) as essential components for the synthesis of propionic acid, the cobalt/iodide catalyst system of the present propionic acid forming processes may contain but do not require such biphyllic ligands. Iodide in excess of that present as ligands in the coordination compound may be used to quarternize the biphyllic ligands if present on the cobalt compound initially charged to the reactor. If preferred, the quaternary salts thus formed may then be removed from the reaction medium prior to the synthesis of propionic acid as taught herein.

With those materials listed above as capable of providing the metal component which do not contain an iodine component, it will be necessary to introduce into the reaction zone such as iodide component. For example, if the cobalt component introduced is cobalt metal or $Co_2O_3$, it will be necessary to also introduce a halide component such as ethyl iodide, hydrogen iodide, iodine or the like.

As noted above, while the iodide component of the catalyst system may be in combined form with the cobalt as for instance, as one or more ligands in a coordination compound, it generally is necessary to have an excess of iodide present in the catalyst system as a promoting component. A critical part of the present invention is the amount of excess iodide used. By excess is meant an amount of iodide greater than 2 atoms of iodide per atom of cobalt in the catalyst system.

The use of excess iodide is critical in prevention of volatilization of cobalt as the carbonyl and decomposition to the metal. Use of iodide to cobalt atom ratios as taught herein of at least 2.1:1 and preferably 2.5:1 prevents such volatization and decomposition of the catalyst both during the reaction and subsequent distillation of the crude propionic acid reaction product for recycle of the soluble cobalt components with iodide present to the reactor. At iodide to cobalt atom ratios less than 2:1 cobalt losses are observed in the effluent gas stream and on the equipment walls resulting in the need for expensive recovery systems or large cost for lost cobalt.

The promoting compound of the catalyst system consists of an iodine and/or iodine compound such as hydrogen, iodide, alkyl or aryl iodide, metal iodide, ammonium iodide, phosphonium iodide, arsonium iodide, stibonium iodide and the like. The iodide of the promoting component may be the same or different from that already present as ligands in the coordination compound of cobalt. Accordingly, suitable iodide providing or promoting components may be selected from the following list of iodine and/or iodide-containing compounds.

| | | | |
|---|---|---|---|
| Co metal | $Co(SnCl_3)[(C_6H_5)_3P]_3$ | | |
| $CoCl_2$ | $Co[(C_6H_5)_3As]_2Cl_2$ | | |
| $CoBr_2$ | $Co[(C_6H_5)_3P]_2Cl_2$ | | |
| $CoI_2$ | $Co(C_5H_5N)_2Cl_2$ | | |
| $CoCl_2.4H_2O$ | $CoO, Co_2O_3$ | RX where R=any alkyl-or | e.g. $C_2H_5I, C_6H_5I$, etc. |
| $CoBr_2.4H_2O$ | $K_3Co(NO_2)_6$ | aryl group (Preferably 1 to 20 carbon atoms | |
| $Co[(C_6H_5)_3P]_2I_2$ | $Co(CH_3CCH\ CCH_3)_2$ $\qquad\ \ \ \| \quad\ \|$ $\qquad\ \ \ O \quad\ O$ | and X=I | |
| $Co[(C_6H_5)_3P]_2I_2$ | | $X_2$ where X=I | e.g. $I_2$ |

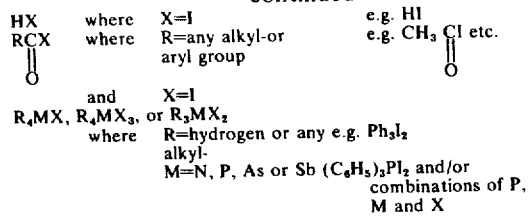

It has been discovered that critical ratios of iodide promoter to active metal catalyst, expressed as atoms of iodide in the promoter portion to atoms of cobalt in the active portion of the catalytic systems, exist. Within the range of these critical ratios, very reactive, non volatile, stable and selective ethylene carboxylation catalyst systems comprised of iodide promoter, and active metal component provided by cobalt precursors, are found that function very efficiently at milder temperatures and pressures than were heretofore possible. The optimum critical ratio of promoter iodide atom as in the range of 2.1:1 to 35:1 for reaction of ethylene, carbon monoxide and water in aqueous carboxylic acid solvent systems. More preferably the range of critical ratios of halide to metal atom employed are 2.5:1 to 25:1.

The existence of this critical ratio of iodide to cobalt is quite unexpected. Thus for the carboxylation of methanol with an iodide-promoted cobalt catalyst the rate has been reported to linearly increase with increasing iodide to cobalt ratio [J. Chem. Soc. Japan (Ind. Chem. Soc.) 65, 1054 (1962]. Hence it is surprising to find that by operating in the narrow range of iodide to cobalt ratios specified herein, it is possible to operate not only with excellent reaction rates but at much lower carbon monoxide pressures than hitherto thought possible with cobalt carboxylation catalysts. All previous reports of cobalt carboxylation catalysts involve the use of high pressures of carbon monoxide. Thus in U.S. Pat. No. 2,448,368, U.S. Pat. No. 2,510,105, British Patent 760,409 and Annalen 582, 38–71 (1953) cobalt catalysts are used for olefin carboxylation and pressures in excess of 3000 psi of carbon monoxide are required in all cases. By contrast, the catalyst systems described herein operate very satisfactorily at pressures less than 1500 psig of carbon monoxide and preferably less than 800 psig of carbon monoxide.

A further advantage is obtained by employing the catalyst system described herein. It is found that by operating within the narrow critical range of iodide promoter to cobalt catalyst specified herein that extremely rapid reaction rates can be obtained at temperatures less than 200°C. By contrast the cobalt catalysts employed in the references cited above require much higher temperatures but even then give slower reaction rates.

Outside the range of critical ratios of iodide to metal atoms, particularly at the higher iodide levels, the reaction efficiency and yield is drastically reduced. For example at the higher iodide levels, significantly higher partial pressure of carbon monoxide is required for the reaction to proceed at an appreciable rate. Also at the higher iodide levels, i.e. higher ratios of iodide to cobalt, e.g. 40:1, the specificity to carboxylic acid product, i.e. propionic acid, is significantly reduced and numerous oxygenated byproducts such as ketones, lactones, aldehydes etc. are formed including oxygenated derivatives of ethylene oligomers of higher molecular weight.

The exact nature of the optimum critical ratio of promoter iodide to metal atom of the catalytic system has not been completely elucidated and may vary as a function of other reaction parameters including solvent composition, absolute concentration of catalyst components, e.g. metal and iodide constituents, and water concentrations.

Generally it is preferred that the process of the present invention be carried out in an acidic reaction medium. For purposes of the present invention, an acidic reaction medium is defined as one in which an alkyl halide is present or will be formed. For example, when the feed is ethylene, the alkyl iodide will be the ethyl iodide. Such alkyl iodide may be added to the reaction medium as such or may be formed in situ within the reaction medium from the ethylene feed and the iodide present in the catalyst system. The reaction medium is considered acidic when under reaction conditions as herein set forth, at least 0.1% by wt. of the total iodide in the system is present as the alkyl iodide.

The preparation of the active catalyst complex which includes both metal and iodide promoter components may be accomplished by a variety of methods. In general, in the process of this invention, it is convenient to preform the active carbonylation catalyst system which contains both metal and iodide promoter components. For example, to prepare the catalyst system, the metal component of the catalyst system, e.g. finely divided cobalt metal (powder), a simple cobalt salt or compound as a precursor is dissolved in a suitable medium, and carbon monoxide is bubbled through the above solution, preferably while maintaining gentle heating and stirring of the solution. Then a solution of the desired iodide promoter source is added to form an active catalytic solution containing the necessary metal and iodide promoter components.

Another embodiment of the present invention employs compounds of divalent cobalt initially- For example, divalent cobalt compounds such as $Co[(C_6H_5)_3P]_2 I_2$ and $Co(pyridine)_2 I_2$ etc. are dissolved in a suitable solvent that is preferably warmed and stirred. Subsequent addition of a solution of the iodide promoter, e.g. alkyl iodide, elemental iodine, aqueous HI etc., results in formation of an active carbonylation catalyst solution.

Alternate embodiments of the present invention include use of other cobalt components in various oxidation states and ligand environments, e.g. metals (zero valence state), cobalt salts, e.g. $CoCl_2$ (+2 valence state), other compounds, e.g. cobalt acetylacetonate (+3 valence state), etc.; with suitable chemical reagents to accomplish the desired transformation of the precursor to an active catalytic complex species. Such reagents include reducing agents, e.g. hydrogen, carbon monoxide, hydrazine, formic acid, phenylhydrazine, etc.; and oxidizing agents, e.g. elemental halogen ($I_2$), mineral acids ($HNO_3$, HI), peroxides ($H_2O_2$, cumene hydroperoxide, etc.).

This catalytic solution containing the necessary metal and iodide components is then ready for use as discussed above, and may be employed as a liquid phase or vapor phase catalyst. As discussed above it is beneficial and desirable to have the concentration of the second component or promoter portion of the catalyst system, for example, iodide such as HI or $I_2$, in excess of that required to form a stoichiometric compound such as described above. In the same way the two components, e.g. a metal compound containing the iodide component may be provided in a single molecule by beginning with metal diiodide as the catalyst precursor for the reaction of ethylene with carbon monoxide and water to produce propionic acid. The present discussion is based upon the catalyst precursors as charged. The ultimate nature of the catalyst as modified by reaction conditions, and the presence of promoters and reactants has not been completely elucidated. However, it has been found that the use of the components as described herein provides a highly superior catalyst and process for the production of propionic acid.

As discussed above the reaction system consists of catalytic amounts of iodide and cobalt components charged in critical ratios as defined herein. The use of catalytic quantities of these two components within critical ratios in the present invention is in contradistinction to prior art processes which employed certain halide promoters in substantially stoichiometric proportion to the olefinic feed, e.g. 1 mole of halide per mole (equivalent) of olefin. As discussed below the critical proportions of iodide-cobalt catalyst system of the present invention results in significantly higher yields of carboxylic acid of the order of 500 to 1,000,000 mole % or more based upon iodide and/or cobalt component charged.

The liquid reaction medium employed may be any solvent compatible with the catalyst system and may include pure olefins or saturated and unsaturated hydrocarbons, e.g. benzene, decane, eicosane, etc. Mixtures thereof with the desired carboxylic acid and/or other carboxylic acids such as nonanoic acid may be used.

The preferred solvent system employed in the present invention in order to achieve a high proportion of propionic acid, rather than the acid anhydride as the product, is based upon the use of an aqueous solution of a carboxylic acid having 2 to 20 carbon atoms as the solvent medium. It has been found that water is essential in the use of the catalyst system.

Although the ethylene-water reaction stoichiometry is 1:1 the preferred catalyst system containing the critical proportions of iodide and cobalt metal component is comprised of an aqueous solution of the carboxylic acid, which may be the same or different from the propionic acid product as discussed above, wherein the water concentration is typically from 0.1% to 25% by weight of the catalyst solution and may vary within the broad range of from 0.1% to 90% by weight. For example in a continuous process a stoichiometric quantity of water equivalent to the number of moles of ethylene reacted(or propionic acid produced) is added continuously to maintain the necessary water concentration of the catalyst solution.

The catalyst system of the present invention is unique in comparison to earlier work in that it does not require the use of anhydrous or highly concentrated mineral acid solutions. Furthermore the present aqueous catalyst system permits the use of iodide sources such as alkyl iodides, e.g. ethyl iodide in place of the highly corrosive mineral acids such as concentrated HI. These factors serve greatly to reduce the corrosivity of the reaction system and make it less necessary to use expensive alloys.

The present invention is based upon the production of propionic acid by the reaction of ethylene, carbon monoxide and water. In accordance with the present invention, the carbonylation reaction may be carried out by intimately contacting gaseous carbon monoxide and water (vapor or liquid) in a liquid phase containing the catalyst system prepared from cobalt precursors; preferably in the presence of iodide containing promoter, such as hydrogen iodide, under conditions of temperature and pressure suitable as described herein to form the carbonylation product. The temperature accordingly will be in the range of 50°C to 300°C with the preferred range being 125°C to 225°C. Partial pressures of carbon monoxide of the order of 1 psia to 1500 psia may be employed; however, 25 psia to 800 psia carbon monoxide partial pressure is generally preferred. Higher pressures may be used if desired under appropriate conditions.

Alternatively, propionic acid may be produced if desired via reaction of ethylene with carbon monoxide and water in the vapor phase over the cobalt containing catalyst systems described above, dispersed upon inert supports. Such a catalyst system may be operated as a conventional fixed bed catalytic reactor. For example, ethylene, aqueous hydrogen iodide, and carbon monoxide may be passed over a catalyst system consisting, for example, of $CoI_2$ dispersed on an inert support material such as alundum, activated carbon, clays, alumina, silicaalumina, and ceramics, etc., in a fixed bed reactor maintained at elevated temperature and pressure, as described above, to produce propionic acid in high yields. However, use of a a liquid reaction medium is preferred in the process of this invention using dissolved or dispersed active catalytic and promoter components.

A typical carbonylation reaction selective to carboxylic acid requires at least one mole of carbon monoxide and one mole of water per mole (equivalent) of ethylene reacted. Excess of carbon monoxide and water as discussed above over the aforesaid stoichiometric amounts, however, may be present. Carbon monoxide streams containing inert impurities such as carbon dioxide, methane, nitrogen, noble gases and paraffinic hydrocarbons having from 1 to 4 carbon atoms, may be employed, if desired, for example from an available plant gas stream, with no ill effect; however, in such cases total reactor pressure will have to be increased to maintain a desired carbon monoxide partial pressure. The concentration of carbon monoxide in the feed gas mixture is from 1 vol. % to 99.9 vol. %, a preferred range being from 10 vol. % to 99.9 vol. %.

The reaction rate is dependent upon catalyst concentration and temperature. Concentrations of the cobalt compound or the first component of the catalyst system in the liquid phase, between $10^{-5}$ moles/liter and 10 moles/liter, are normally employed, with the preferred range being $10^{-2}$ moles/liter to 1 mole/liter. Higher concentrations even to the extent of 10 moles/liter may, however, be used if desired. Higher temperatures also favor higher reaction rates.

The concentration of the second component or promoter portion of the catalyst system may vary widely over the broad concentration range of $10^{-6}$ moles/liter to 18 moles/liter, based on iodide atoms. In the process of this invention, however, the preferred critical range of ratios of iodide atoms to metal atoms must be maintained as discussed herein to achieve the superior results.

The active catalytic component is preferably supplied as a catalyst solution. The solution can also include liquid reactants, products and mixtures thereof which function as solvents or reaction media.

The ethylene feedstock is normally charged with equimolar amounts of water, although more or less water may optionally be used.

For example in a batch reactor system when ethylene and carbon monoxide are fed in a stoichiometric excess to water some propionic anhydride may be co-produced with propionic acid. Subsequent addition of water to the reactor system or product during isolation steps will convert the anhydride to acid resulting in a substantially quantitative yield of propionic acid.

The iodide promoted cobalt catalysts of the present invention are characterized by a high degree of specificity for the carboxylation reaction, e.g., the reaction of ethylene with carbon monoxide and water to obtain propionic acid selectively. Such control over the various competing reactions to obtain the carboxylic acid in a very high yield selectively is surprising since other Group VIII metal catalysts promoted by iodide do not show such specificity. Other Group VIII metal catalysts containing high concentrations of halide promoter, e.g., iron, nickel, rhodium with high halide levels, differ from the present catalysts in that they also produce a number of oxygenated products such as alcohols, aldehydes, lactones, esters and ketones in addition to carboxylic acid.

For a better understanding of the process of the present invention specific embodiments of the process are presented below. These examples and illustrations are not to be constructed in any way as limiting the scope of the invention.

EXAMPLE 1

A batch reactor is charged with the following ingredients: 3.2 grams ($1 \times 10^{-2}$ moles) of a cobalt compound having the formula $CoI_2$, as catalyst precursor; 3.1 gms. (0.02 moles) of a promoter component consisting of ethyl iodide; 85 ml of propionic acid and 4.0 ml $H_2O$ as solvent; the olefin feed, ethylene, is charged to the reactor as a 1:1 molar mixture with carbon monoxide. The ratio of I/Co is 4:1.

The reactor is pressurized with the gas blend to a total pressure of 1000 psig, (p. press of CO about 475 psi) at 195°C. The reaction is carried out at constant pressure by feeding the gas blend upon demand, from a high pressure reservoir. Reaction time is 2⅔ hours.

The reaction mixture subsequently analyzed by gas chromatographic technique, yields a solution containing:

94.2 wt % propionic acid
0.2 wt % miscellaneous intermediates including halides 5.5 wt % ethyl iodide and ethyl propionate The selectivity to propionic acid (produced from ethylene) is greater than 99%. No other organic oxygenated compounds such as alcohols, aldehydes, ketones, lactones, etc., are produced from the olefin feed as determined by gas chromatographic analysis. No substantial amounts of other undesirable byproducts such as methane, carbon dioxide, or higher olefin derivatives and/or higher acids are formed.

The rate of reaction varies somewhat during the reaction time in the batch system due to the change in reactant concentrations. However, it has been found that the total gas consumption measured by decrease in pressure of the feed reservoir during the reaction time is an excellent representation of catalyst system reactivity. For comparison purposes in this example and those that follow the gas consumption is expressed in terms of total amount of gas feed mixture consumed at constant reaction time i.e. $\Delta$psi/1 hour of reaction. For the 4:1 iodide/cobalt atomic ratio of this example the $\Delta$psi/hour is 750 psig equivalent to 0.135 mole of propionic acid produced. Average reaction rate during the hour is 1.5 gram-moles of propionic acid/liter-hr with a maximum reaction rate of 2.0 gram-mole of propionic acid/liter-hr.

Based on the number of moles of halide promoter charged to the reactor the molar yield of propionic acid is greater than 340% during the batch reaction.

In this and subsequent examples reaction rates have been maintained slow and conversion low in order to more clearly demonstrate the concept of critical ratio.

At the 4:1 iodide to cobalt atom ratio of this example and at other critical ratios claimed herein a stable catalyst system exists i.e. no cobalt metal precipitation. Moreover no volatile cobalt compounds are observed in the reactor off-gas or in the vapor from distillation of the reaction product. Thus the cobalt is recycled to the reactor without expensive metal recovery from the vapor or from the metal deposited on the equipment walls due to decomposition of the cobalt carbonyl.

EXAMPLE 2

Using similar experimental conditions as in Example 1 except increasing the iodide/cobalt ratio to 15:1 (feed contains 20 grams of ethyl iodide) the catalyst system reactivity is substantially lower. For the 15:1 iodide to cobalt atomic ratio the $\Delta$psi/hour is 120 psi equivalent to 0.02 moles of propionic acid produced. Average reaction rate during the hour is 0.2 gram-moles of propionic acid/liter-hr, less than 15% of the reactivity of Example 1 at a lower iodide/cobalt ratio. The maximum reaction rate observed in Example 2 is only 0.25 gram-moles/liter-hr also less than 15% of the catalyst system reactivity in Example 1.

EXAMPLE 3

The experiment of Example 2 is repeated but at a higher iodide/cobalt ratio of 25:1. For the 25:1 iodide cobalt atomic ratio the $\Delta$psi/hr is 195 psi equivalent to 0.035 moles of propionic acid produced. Average reaction rate during the hour is 0.3 gram-moles of propionic acid/liter-hr. The maximum reaction rate observed is 0.32g-m/l-hr again considerable less than at the 4:1 ratio of Example 1.

EXAMPLE 4

Using similar conditions as in Example 1 except decreasing the iodide/cobalt atomic ratio to 1:1 (reaction charge contains 2.5 grams of cobalt(II)acetate plus 1.6 grams of ethyl iodide) the catalyst system reactivity is substantially lower. For the 1:1 iodide to cobalt atomic ratio the $\Delta$psi/hour is 150 psi equivalent to 0.027 moles of propionic acid produced. Average reaction rate during the hour is 0.3 gram-moles/liter-hour, less than 20% of the reactivity of Example 1 at a higher iodide/cobalt ratio. The maximum reaction rate observed in Example 4 is only 0.36 gram-moles/liter-hour also less than 20% of the catalyst system reactivity at 4I/Co.

At the 1:1 iodide to cobalt ratio of this example, which lies below the critical ratios claimed herein, volatilization of cobalt, probably as the carbonyls, is observed. Thus upon releasing the reactor gas pressure in order to remove the liquid product, greater than 25% of the original cobalt charged to the reactor is lost. In the previous three examples at ratios within the critical range less than 2% of the originally charged cobalt is lost even after distillation of the crude reaction product for recycle of the cobalt in the distillate heel. Furthermore no significant cobalt plating is observed during this distillation in Examples 1 to 3. At the 1:1 iodide to cobalt ratio of Example 4 when an appreciable portion of the cobalt is present as a carbonyl, cobalt metal plating occurs upon distillation of the reaction product with a corresponding loss of cobalt.

Using similar experimental conditions as in Example 1 except varying catalyst components i.e. metal precursor, e.g. $Co(NO_3)_2$, cobalt octanoates, cobalt metal, and/or form of iodide (e.g. aqueous HI, propyl iodide, calcium iodide), catalyst concentration, operating pressure and temperature, water concentration, solvent (e.g. octane, acetic acid, benzene) produces a similar reactivity relationship with respect to the iodide to cobalt atomic ratio.

In FIG. 1 the reactivity of the catalyst system in terms of gram-moles of propionic acid produced per liter-hour is plotted versus iodide/cobalt ratio. The dotted line is for the experimental conditions and cobalt concentrations of Examples 1 through 4. The cross-hatched area corresponds to the range of other typical results for reactivity versus I/Co ratio obtained for variations in catalyst concentration, operating conditions, water level and solvent.

FIG. 1 demonstrates that an optimum reactivity occurs in the propionic acid synthesis with respect to I/Co ratio. At iodide to cobalt ratios higher than the ratios claimed herein a drastic decrease in reactivity to propionic acid occurs. In addition at ratios greater than 35 I/Co the reaction is observed to be less than stoichiometric in iodide.

EXAMPLE 5

To demonstrate that ethylene is a uniquely reactive feedstock at the mild operating conditions and critical iodide/cobalt ratios employed, ethylene is replaced by hexene-1 at the experimental conditions of Example 1. No reactivity of the hexene-1 to heptanoic acid is observed either by carbon monoxide uptake or gas chromatographic analysis of the reaction product.

When hexene-1 is replaced by other olefins (e.g. propylene, octene-1) or di-olefins (e.g. butadiene) at the same conditions no reactivity to the corresponding carboxylic acids occurs.

EXAMPLE 6

In this and the subsequent examples the common metals (e.g. Ni, Rh, Ir) previously reported to catalyze the hydrocarbonylation of ethylene to propionic acid employing an iodide promoter are investigated with respect to critical iodide/metal ratio. In Example 6 nickel is run at the identical 4:1 iodide to metal ratio of Example 1 (i.e. 3.2 grams $NiI_2$ and 3.1 grams of ethyl iodide), metal concentration (i.e. $1 \times 10^{-2}$ moles) and operating conditions. For the 4:1 iodide to nickel atomic ratio the $\Delta$psi/hour is 245 psi equivalent to 0.044 moles of propionic acid produced. Average reaction rate during the hour is 0.46 gram-moles/liter-hour, less than one-third of that of Example 1 with cobalt. The maximum reaction rate observed in Example 6 is only 0.5 gram-moles/liter-hr, less than 25% of that in Example 1.

EXAMPLE 7

A drastic difference is observed for the nickel/iodide catalyst system versus the cobalt/iodide catalyst system, moreover, as the iodide/nickel ratio is varied. For cobalt, the reaction rate drops significantly at less than the stoichiometric composition of $CoI_2$ (i.e. 2 I/Co). The preferred ratio as taught herein is excess of iodide above 2 I/Co. Employing the reaction conditions of Example 6 but decreasing the iodide to nickel atomic ratio to less than 2 I/Ni(i.e. 2.5 grams Ni(II) acetate and 1.6 grams ethyl iodide for a 1:1 Ni to I ratio) results in an opposite effect to that for cobalt. Instead of decreasing as with cobalt, the nickel catalyzed reaction rate relative to Example 6 increases as demonstrated by the gas uptake doubling to a $\Delta$psi/hour of 500 psi equivalent to 0.09 moles of propionic acid produced. In addition, the average reaction rate during the hour increases to 0.95 gram-moles/liter-hour.

Whereas comparing Examples 1 and 6 at atomic ratio of 4I/metal above shows the reaction rate with nickel is less than one-third that of cobalt, the comparison of Examples 4 and 7 at an atomic ratio of 1 iodide/metal atom shows the reaction rate with nickel is more than double that of cobalt.

Figure 2:
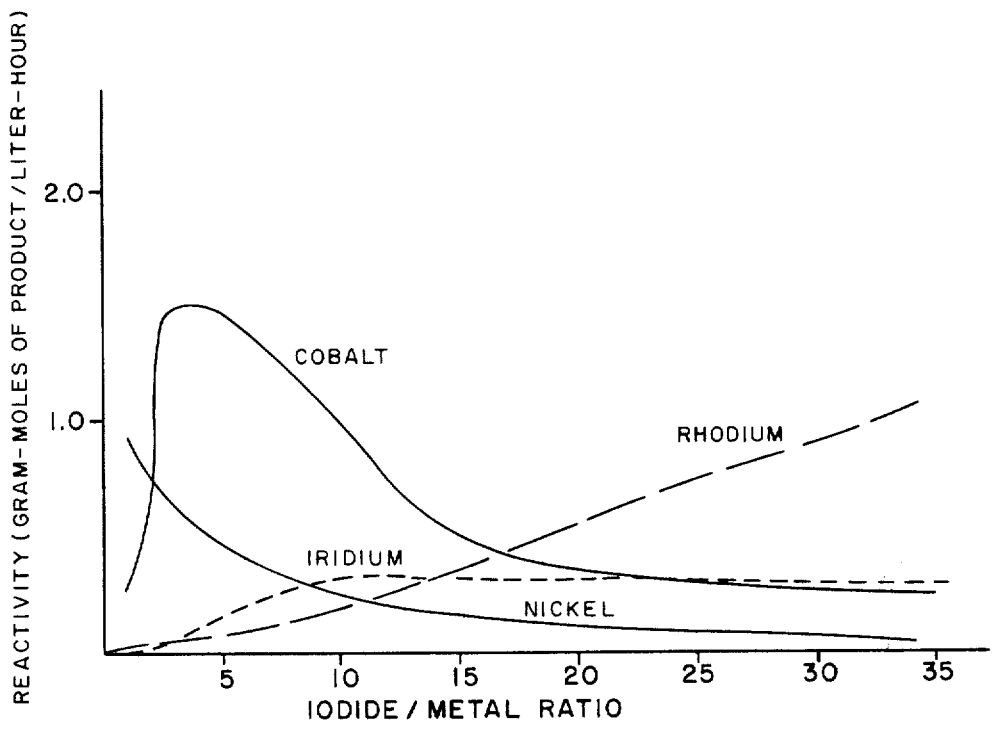

In FIG. 2 the reactivity of nickel at other iodide to nickel ratios is shown in comparison to cobalt. The figure clearly demonstrates the following:

1. nickel and cobalt, metals which would be expected to behave catalytically quite similarly, in fact behave very differently with respect to iodide/metal ratio for the hydrocarbonylation of ethylene to propionic acid.

2. the nickel iodide catalyst system is best operated with small additions of iodide, less than that required to form the stoichiometric $NiI_2$ e.g. outside of the presently claimed range for cobalt. Higher ratios of iodide to nickel result in a drastic slow down in catalyst system reactivity. This result is consistent with the prior art which teaches $Ni(CO)_4$ as a preferred catalyst for ethylene hydrocarbonylation with promoting of the reaction by small quantities of iodide, always less than 2 Iodide per nickel and generally less than 1 iodide per atom of nickel.

3. Cobalt has an optimum reactivity with respect to iodide/cobalt ratio. At both low and high iodide to cobalt ratios, reactivity of the catalyst system decreases. However, for a nickel catalyst, reactivity steadily decreases as the iodide to metal atomic ratio increases.

EXAMPLE 8

At comparable operating conditions to Example 1 rhodium is employed as the catalytic metal for the hydrocarbonylation of ethylene to propionic acid. Iodide to rhodium ratio is varied as in the preceding examples. The results are presented in FIG. 2. The results demonstrate that:

1. Cobalt and rhodium which are elements of the same row of the Periodic Table, behave very differently with respect to iodide/metal ratios for the hydrocarbonylation of the ethylene to propionic acid, rhodium requiring considerably higher iodide to metal ratios.

2. Over the critical ratios of iodide/metal at which cobalt is operable, rhodium is still far from its optimum reactivity. In fact the rhodium/iodide catalyst system is most reactive at ratios of 50 to 100 I/metal atom ratio, and is catalytic up till as high as 350 I/Rh. This is ten times as high a ratio as that for which cobalt is catalytic in iodides (above a ratio of 35 iodide per cobalt, the hydrocarbonylation of ethylene is observed to be less than stoichiometric in iodide as demonstrated by the molar yield of propionic acid being less than 100% based on iodide charged).

EXAMPLE 9

At comparable operating conditions to Example 8, iridium is employed as the catalytic metal in place of rhodium, and the ratio of iodide to iridium is varied. The results are presented in FIG. 2. Again the reactivity versus iodide/metal atomic ratio is quite unpredictable. With rhodium very high iodide to metal ratios are required. One might expect this also to be true for iridium since it is below rhodium in the Periodic Table, but a considerable difference occurs, as shown in the drawing. FIG. 2 shows that the effective ratios for iridium are between those for cobalt and rhodium.

It is clear therefore that each of the metals investigated (e.g. Ni, Rh and Ir) behave uniquely and very differently from cobalt with respect to the relationship between reactivity versus iodide/metal ratio.

What is claimed is:

1. A one step, low-pressure process for the preparation of propionic acid which comprises reacting ethylene with carbon monoxide and water at a temperature of 50°C to 300°C and a partial pressure of carbon monoxide of from 1 to 1500 psia in the presence of
   1. a cobalt component;
   2. an iodide component wherein the range of atomic ratios of said iodide to cobalt is from 2.1:1 to 35:1.

2. A one step, low-pressure process for the preparation of propionic acid which comprises reacting ethylene with carbon monoxide and water at a temperature of 50°C to 300°C and a partial pressure of carbon monoxide of from 1 to 1500 psia in the presence of
   1. a cobalt component;
   2. an iodide component wherein the range of atomic ratios of said iodide to cobalt is from 2.1:1 to 35:1, the said catalyst system existing as an aqueous solution of a carboxylic acid having from 2 to 20 carbon atoms, the said aqueous solution containing from 0.1% to 25% by weight of water.

3. A one step, low-pressure process for the preparation of propionic acid which comprises reacting ethylene with carbon monoxide and water at a temperature of 50°C to 300°C and a partial pressure of carbon monoxide of from 1 to 1500 psia in the presence of
   1. a cobalt component;
   2. an iodide component, wherein the range of atomic ratios of said iodide to cobalt is from 2.5:1 to 25:1.

4. A one step, low-pressure process for the preparation of propionic acid which comprises reacting ethylene with carbon monoxide and water at a temperature of 50°C to 300°C and a partial pressure of carbon monoxide of from 1 to 1500 psia in the presence of
   1. a cobalt component;
   2. an iodide component, wherein the range of atomic ratios of said iodide to cobalt is from 2.5:1 to 25:1, the said catalyst system existing as an aqueous solution of a carboxylic acid having from 2 to 20 carbon atoms, the said aqueous solution containing from 0.1: to 25% by weight of water.

5. A process as in claim 1 in which the partial pressure of carbon monoxide is from 25 psia to 800 psia.

6. A process as in claim 2 in which the partial pressure of carbon monoxide is from 25 psia to 800 psia.

7. A process as in claim 1 in which the iodide component is ethyl iodide.

8. A process as in claim 2 in which the iodide component is ethyl iodide.

9. A process as in claim 1 in which the cobalt component is cobalt iodide.

10. A process as in claim 2 in which the cobalt component is cobalt iodide.

* * * * *